(12) United States Patent  (10) Patent No.: US 7,906,971 B2
Boardwine et al.  (45) Date of Patent: Mar. 15, 2011

(54) MOLECULAR SHIELD FOR AN IONIZATON VACUUM GAUGE

(75) Inventors: Benjamin Aaron Boardwine, New Castle, VA (US); Derrick Lamont Journiette, Roanoke, VA (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 254 days.

(21) Appl. No.: 12/250,785

(22) Filed: Oct. 14, 2008

(65) Prior Publication Data

US 2010/0090703 A1 Apr. 15, 2010

(51) Int. Cl.
*G01L 21/30* (2006.01)
(52) U.S. Cl. .................................. 324/460; 324/463
(58) Field of Classification Search .................. 324/459, 324/460, 464; 313/7; 315/108
See application file for complete search history.

(56) References Cited

U.S. PATENT DOCUMENTS

| 2,605,433 | A | | 7/1952 | Bayard |
| 3,320,455 | A | * | 5/1967 | Whetten et al. .................... 313/7 |
| 3,387,175 | A | * | 6/1968 | Lloyd et al. .................... 315/108 |
| 6,515,482 | B2 | | 2/2003 | Kawasaki |
| 7,030,620 | B2 | | 4/2006 | Correale |
| 7,295,015 | B2 | | 11/2007 | Arnold et al. |
| 2008/0100301 | A1 | | 5/2008 | Knott |

OTHER PUBLICATIONS

S.F. Belykh and V. V. Palitsin, "New Cs Sputter Ion Source with Polyatomic Ion Beams for Secondary Ion Mass Spectrometry Applications", Review of Scientific Instruments 78, 085101-1-085101-9 (2007).
Robert L. Summers, "Effects of Cesium Vapor on Bayard-Alpert Ionization Gages at Pressures Less than $10^5$ TORR", NASA Technical Note, National Aeronautics and Space Administration, Washington, D.C., Mar. 1964.
Stanford Research Systems, "Select The Best Bayard-Alpert Ionization Gauge for your Application", www.thinkSRS.com, pp. 1-10, Oct. 14, 2008.
WIKIMEDIA Commons, Image: Bayard-Alpert gauge.jpg, http://commons.wikimedia.org/wiki/Image:Bayard-Alpert: guage.jpg, Jul. 28, 2008.

* cited by examiner

*Primary Examiner* — Vincent Q Nguyen
(74) *Attorney, Agent, or Firm* — RatnerPrestia

(57) ABSTRACT

A system for measuring gas density in a vacuum includes a gauge, a housing for containing the gauge, and a magnet secured to an exterior surface of the housing. The magnet is a flexible magnetic strips, and positioned around the exterior surface of the housing. The gauge includes grid insulator posts extending longitudinally along a tubular section of the housing, and the magnet is secured to the exterior surface of the housing adjacent to the grid insulator posts, and oriented transversely to the grid insulator posts. The magnet is a flexible magnetic strip, and a clamp secures the magnet to the exterior surface of the housing.

9 Claims, 4 Drawing Sheets

MOLECULAR SHIELD FOR AN IONIZATON VACUUM GAUGE

FIELD OF THE INVENTION

The present invention relates, in general, to ionization vacuum gauges. More specifically, the present invention relates to redirecting contaminants away from ionization vacuum gauges.

BACKGROUND OF THE INVENTION

Ionization vacuum gauges may be used to measure low pressures of gases. Ionization vacuum gauges sense pressure indirectly by measuring the electrical ions produced when a gas is bombarded with electrons.

Ionization vacuum gauges may include the following types: (1) thermionic emission vacuum gauges, also called hot cathode vacuum gauges; and (2) field emission vacuum gauges, also called cold cathode vacuum gauges. In hot cathode vacuum gauges, an electrically-heated filament produces an electron beam. The electrons travel through the gauge and ionize gas molecules around them. The resulting ions are collected at a negative electrode. The current flowing through the electrode depends on the number of ions, which depends on the gas pressure in the gauge. The principle behind cold cathode vacuum gauges is the same, except that electrons are produced in a discharge created by a high voltage electrical discharge.

A typical example of a hot cathode vacuum gauge is the Bayard-Alpert vacuum gauge disclosed in U.S. Pat. No. 2,605,431, issued to Bayard on Jul. 29, 1952, which is incorporated herein by reference in its entirety.

The Bayard-Alpert type ionization vacuum gauge is the most common non-magnetic gauge for measuring very low pressures and has been widely used worldwide. The Bayard-Alpert vacuum gauge ionizes the gas molecules within the gauge volume, collects those ions on a thin ion collector wire and measures the resulting current in the ion collector wire. The number of gas molecules present in the volume, or the pressure in the volume, may be determined based on the current measurement.

The Bayard-Alpert gauge may include at least one heated filament that emits electrons toward an anode, for example a cylindrical wire grid. At least one ion collector electrode is placed within and along the axis of the cylindrical wire grid. The negative electrons, which are emitted from the heated filament (a cathode), are accelerated toward the positively-charged cylindrical wire grid (an anode). Electrons pass into the volume of space enclosed by the cylindrical wire grid. In this volume, the electrons collide with any gas molecules in the vacuum chamber and, thereby, produce positive ions. These positive ions are collected by the ion collector electrode disposed within the cylindrical wire grid.

The ion collector electrode may be at nearly ground potential and may be negative compared to the cylindrical wire grid. At constant filament-to-grid voltage and electron emission current, the rate that the positive ions are formed is directly proportional to the density of molecules (pressure) in the vacuum gauge for pressures below about $1 \times 10^{-3}$ Torr. The strength of the current may be indicated on a meter, which may be calibrated in units of pressure.

Vacuum chambers requiring very low pressures are used in many different processes. For example, some processes performed in a vacuum chamber produce metallic evaporates. These processes, however, contaminate the ion gauge which is used to measure the pressure in the chamber.

The present invention provides a method and apparatus for reducing the contaminants reaching the ion gauge collector. By directing the contaminants away from the ion gauge collector, as will be described, the ion gauge has less of a likelihood for being damaged, is more accurate, and has a longer maintenance-free life cycle, and is more accurate.

SUMMARY OF THE INVENTION

To meet this and other needs, and in view of its purposes, the present invention provides a system for measuring gas density in a vacuum including a gauge, a housing for containing the gauge, and a magnet secured to an exterior surface of the housing. The magnet is a flexible magnetic strip, and positioned around the exterior surface of the housing.

The gauge includes grid insulator posts extending longitudinally along a tubular section of the housing, and the magnet is secured to the exterior surface of the housing, adjacent to the grid insulator posts, and oriented transversely to the grid insulator posts. The magnet is a flexible magnetic strip, and a clamp secures the magnet to the exterior surface of the housing. The magnet is formed from a high temperature material, and the clamp is formed from stainless steel and is adjustable to press fit the magnet around the exterior surface of the tubular section of the housing.

Another embodiment of the present invention is a vacuum gauge including an ion collector wire extending longitudinally in a tubular section of a housing; a filament extending longitudinally along and spaced from the ion collector; a grid surrounding the ion collector wire; grid insulators extending longitudinally in the tubular section of the housing including electrical conductors for providing a voltage potential to the grid; and a magnet disposed externally to the tubular section of the housing. The magnet is a flexible magnetic strip, and positioned around the exterior of the tubular section of the housing. The magnet is secured transversely to the grid insulators on the exterior of the tubular section of the housing. A clamp provides a press fit for the flexible magnetic strip around the exterior of the tubular section of the housing. The flexible magnetic strip is oriented transversely and adjacent to the grid insulators. The flexible magnetic strip may include a plurality of magnetized strips oriented circumferentially around the exterior of the tubular section of the housing.

Yet another embodiment of the present invention is a method of reducing metallic contamination of a Bayard-Alpert vacuum gauge including grid insulator posts. The method includes the steps of: (a) exposing the Bayard-Alpert vacuum gauge to metallic vapor; and (b) providing a magnetic field adjacent to the grid insulator posts. The magnetic field is effective in reducing metallic deposits on the grid insulator posts.

The step of providing the magnetic field includes attaching a flexible magnetic strip on an exterior surface of a housing surrounding the Bayard-Alpert vacuum gauge. The flexible magnetic strip is attached transversely to and adjacent to the grid insulator posts.

The attaching step includes clamping the flexible magnetic strip using an adjustable stainless-steel hose clamp. Providing the magnetic field includes providing a magnetic field having a strength of at least 160 gauss.

BRIEF DESCRIPTION OF THE FIGURES

The invention may be best understood from the following detailed description when read in conjunction with the accompanying figures.

DETAILED DESCRIPTION OF THE INVENTION

Many processes require a vacuum chamber for depositing a metallic substance onto a surface of a substrate. During the process, metallic vapor is combined with oxygen in a vacuum forming a metallic oxide. The metallic oxide, however, contaminates the ionization vacuum gauge used for measuring the vacuum pressure of the chamber, in which the substrates are processed. The inner components of the ionization gauge are exposed to the vacuum and, consequently, become coated with metallic evaporates.

As described below, the present invention provides a method and apparatus for directing contaminants, such as a metallic vapor, away from the inner components of the ionization gauge.

Figure 1:
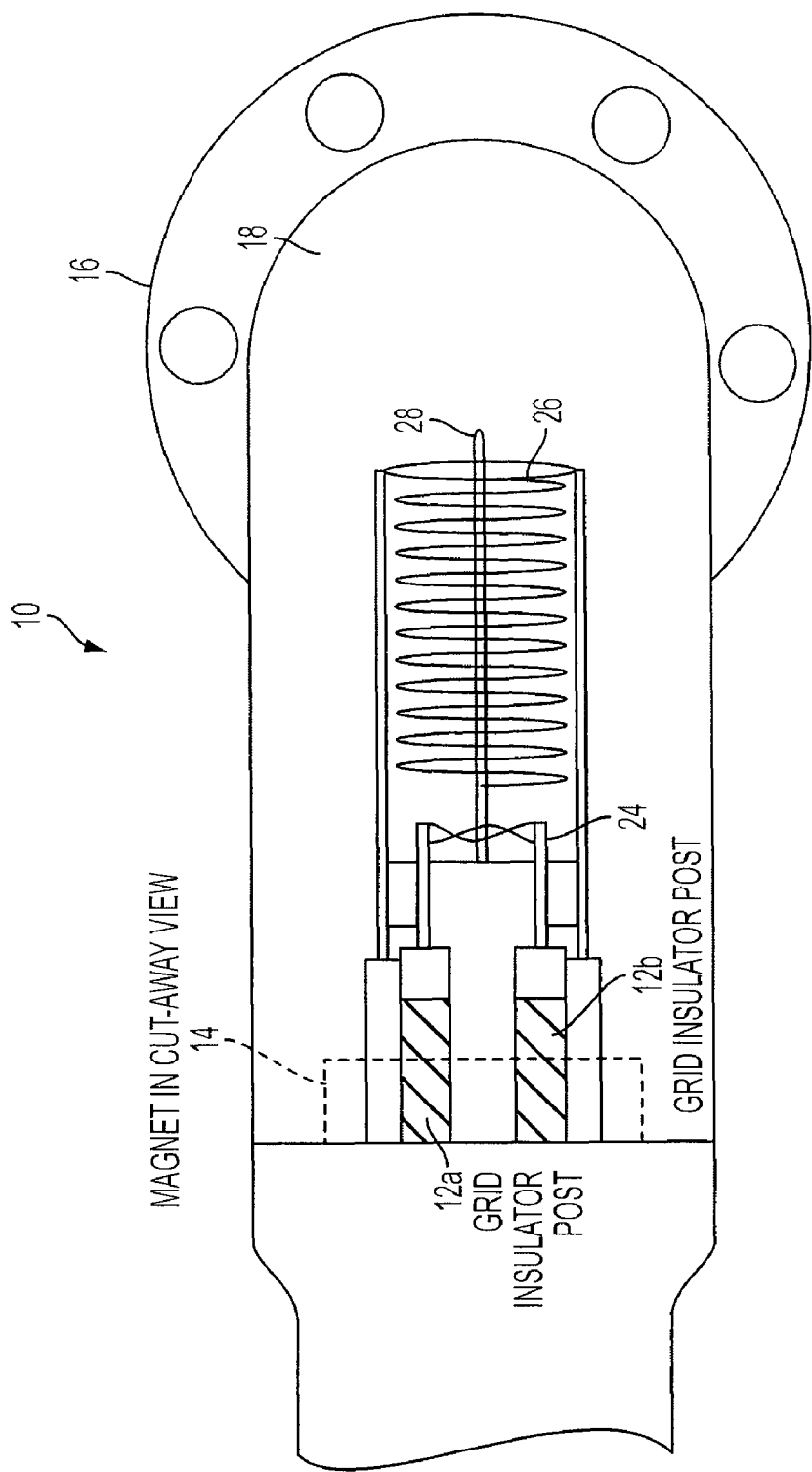
FIG. 1 is a cut-away, top view of a right angle ionization vacuum gauge with a molecular shield installed in accordance with an embodiment of the present invention.
Figure 2:
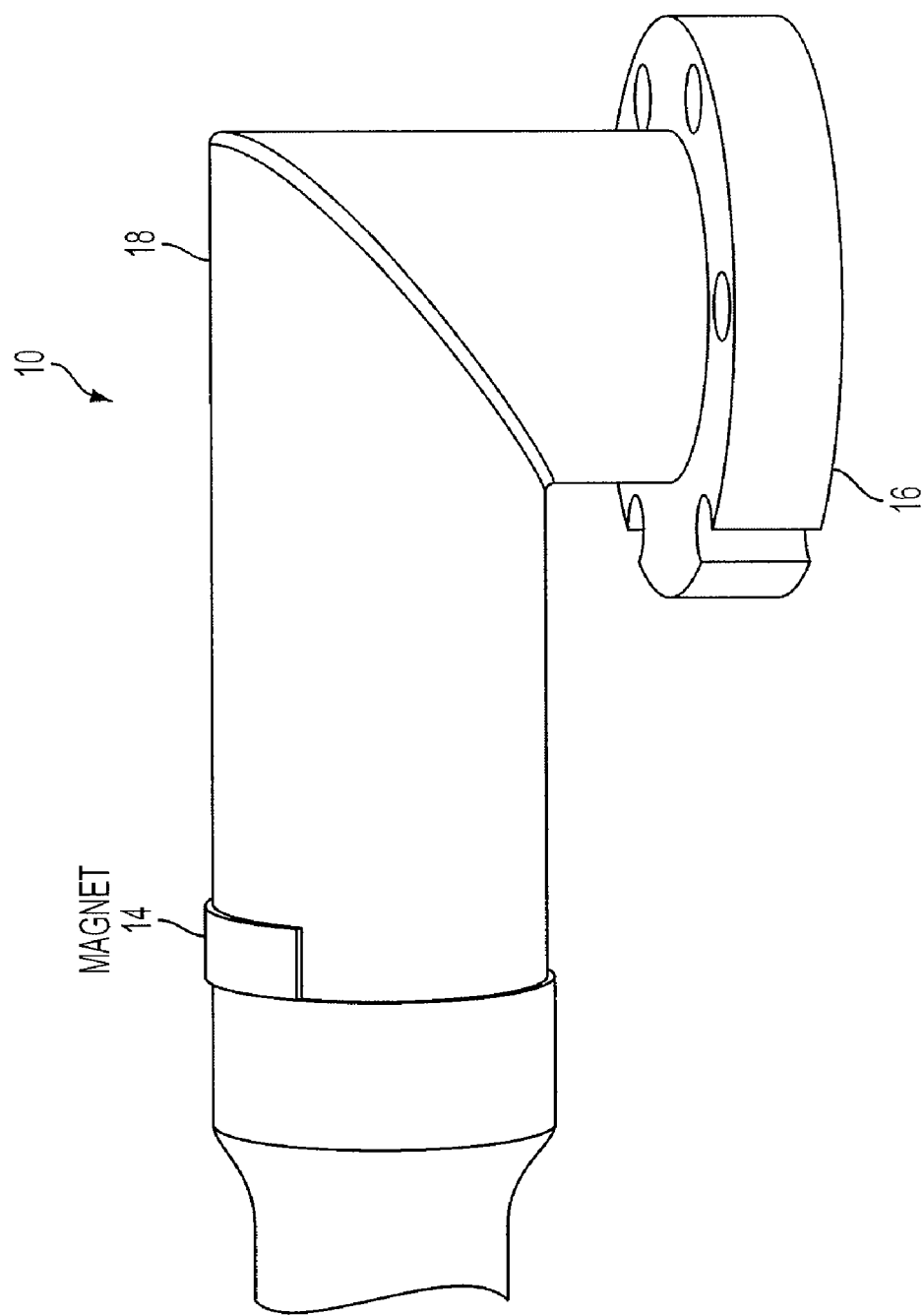
FIG. 2 is a side view of a housing for the right angle ionization vacuum gauge shown in FIG. 1, with the molecular shield installed in accordance with an embodiment of the present invention.
Figure 3:
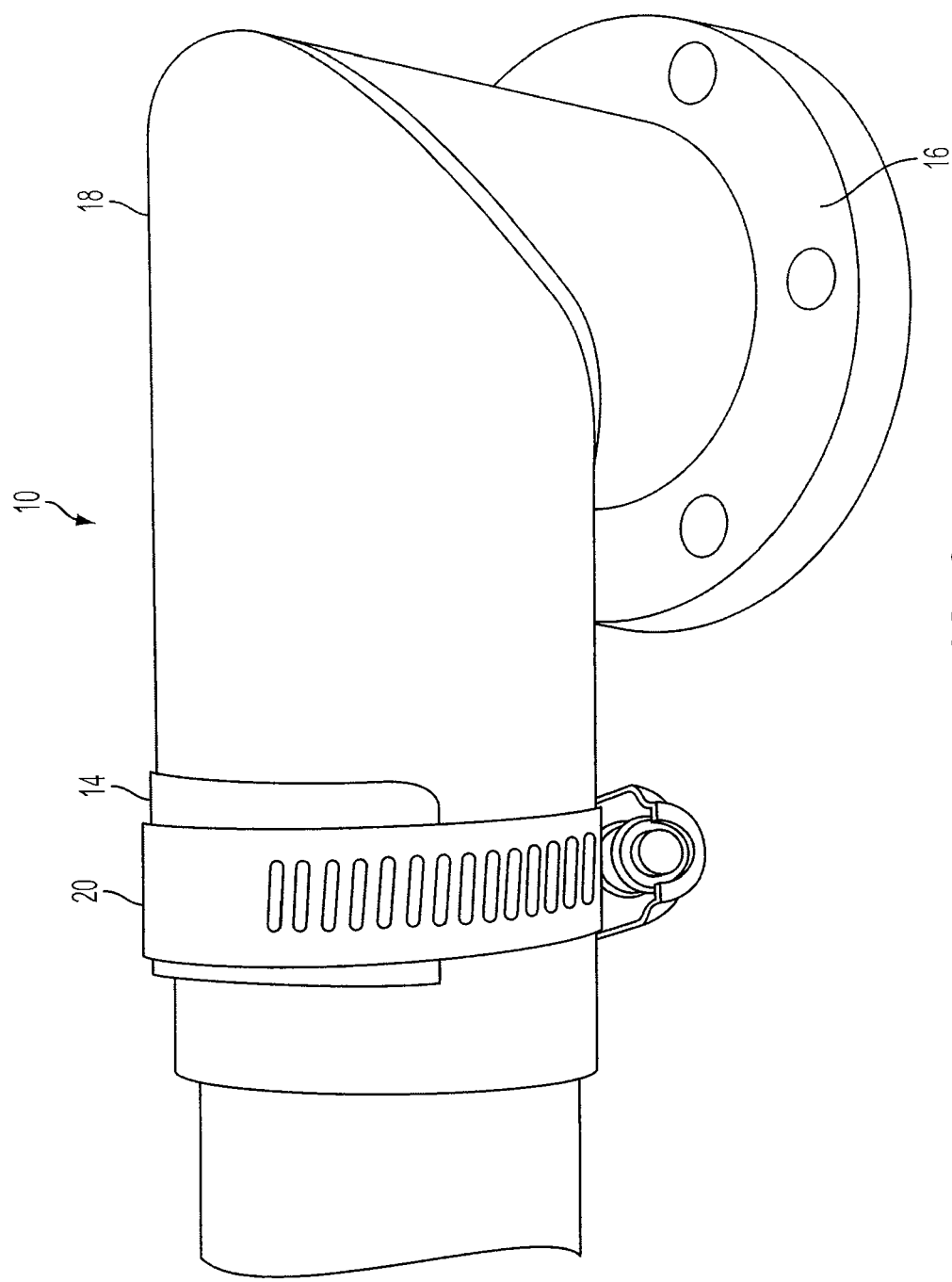
FIG. 3 shows a clamp for securing the molecular shield around the housing of the right angle ionization vacuum gauge of FIG. 2, according to one exemplary embodiment of the invention.

Referring to FIGS. 1, 2 and 3, there is shown a right angle ionization vacuum gauge, generally designated as 10. The ionization vacuum gauge may be a Bayard-Alpert gauge, as shown in a top cut-away view of FIG. 1. The Bayard-Alpert gauge includes tungsten filaments (cathode) 24, helical coil grid (anode) 26, and collector wire (ion collector) 28.

There are two types of materials commonly used for filaments: tungsten and iridium. There are two types of coatings used on the filaments: thoria and yttria.

Generally, filaments are yttria-coated iridium, thoria-coated iridium, or uncoated tungsten. The most common style is coated iridium, because they operate at a lower temperature than tungsten, and therefore, are less reactive. Coated iridium filaments are also more burnout resistant, when exposed to atmospheric pressure while power is on. Tungsten filaments will burn out immediately if exposed to pressures of $1 \times 10^{-2}$ Torr or higher, while they are on. However, tungsten filaments are the best type to use, when the chemistry (such as halogen compounds) of the vacuum process causes premature failure of coated iridium filaments.

The amount of emission current that a Bayard-Alpert gauge requires for proper operation depends on many factors such as: the type of filament, the size or style of the gauge, the process in which the gauge is used, the pressure range of operation, and the desired sensitivity of the indicated pressure. Emission currents are typically in the range of 25 μA to 10 mA.

Also shown in the cut-away view of FIG. 1 are the grid insulator posts, designated 12a and 12b, which support and insulate the grid conductors, while they are positively charged with respect to filaments 24. Although not shown, input/output (I/O) pins are connected to the grid conductors for providing a voltage potential to helical coil grid (anode) 28. The input/output pins are shown in cross-section in FIGS. 4A and 4B, designated as 40a and 40b.

It will be understood that FIG. 1 shows one example of an ionization gauge. There are many other types of ionization gauges, in which the anode, cathode and ion collector have configurations different than the configuration shown in FIG. 1. For example, an ultrahigh vacuum (UHV) nude Bayard-Alpert gauge may be used to measure pressure below $2 \times 10^{-11}$ Torr. This lower limit is achieved by modifying two elements of a standard Bayard-Alpert gauge. First, the diameter of the collector is reduced. The smaller cross-sectional area reduces the probability that x-rays created at the grid will strike the collector. Second, the helical grid structure is replaced with a fine-wire mesh grid structure, and there is also a fine-wire structure across both ends of the grid. The fine grid wires provide a more transparent grid for longer electron path lengths, and the grid ends confine the positive ions for better ion collection. Together, these two modifications cause a higher gauge sensitivity.

Returning to FIG. 1, at an end distal from grid insulator posts 12a, 12b, tubular housing 18 includes a right angle bend that continues the tubular section of housing 18 and terminates in a connecting flange, designated as 16. The connecting flange may be coupled to a pressure chamber (not shown), in which metallic evaporation may be produced during processing of substrates (for example).

The connecting flange 16 includes a tubular opening (not shown) in tubular housing 18. This tubular opening permits gas from the pressure chamber to be introduced into the interior of housing 18 for pressure measurement by ionization gauge 10.

Since the tubular opening of gauge housing 18 permits metallic vapor to enter the ionization chamber, the present invention provides a molecular shield for a Bayard-Alpert type ionization gauge. The molecular shield reduces contamination of the ionization gauge elements (namely, the filament (cathode), the coil grid (anode), the collector wire and the grid insulators, due to metallic evaporates.

One exemplary embodiment of a molecular shield is shown in FIGS. 1, 2, 3 and 4A, including magnet 14. As shown, magnet 14 is a thin, flexible high-temperature magnet having dimensions of approximately 2.25 inches long by 1.0 inches wide, and 0.5 inches high. The magnet 14 is wrapped around a portion of the outer surface circumference of tubular housing 18.

The magnet 14 is positioned directly over internal grid insulator posts 12a, 12b in a direction transverse to the longitudinal direction of the grid insulator posts. The magnet 14 may be fastened around the outer surface of tubular housing 18 using any fastener. As shown in FIG. 3, the flexible magnetic strip is fastened to housing 18 using a 2.25 inch stainless hose clamp, designated as 20. The magnet 14 is fastened to housing 18, as shown, over a portion of the circumference that is closest to the grid insulator posts.

The inventor has discovered that the resulting magnetic field created by magnetic strip 14 acts as a shield surrounding the collector and grid insulator posts. When molecules of a metallic vapor come near the field, they are redirected away from the grid insulators, before the metallic vapor adheres to the grid insulators and causes premature gauge failure due to current leakage to ground.

It will be appreciated that the magnet may be made of any material, so long as the effective magnetic gauss intensity and the pole orientation are similar. The magnet may be made from a rigid magnetic material, if the curvature of the magnetic strip is manufactured to fit the circumferential curvature of the tubular section of housing 18.

Furthermore, the strength of the magnetic strip is dependent upon the thickness of housing 18 which typically is made from stainless steel. The strength of the magnetic field produced by magnet 14 must be sufficient to enter the interior of housing 18. The minimum strength of the magnet is 160 gauss.

The magnet may include a dry mixture of ferrite powder and rubber polymer resin, which is mixed, calendered and ground. The ground mixture may then form a strip. It is then magnetized.

The magnet must be of a high temperature component, so that the magnet may withstand temperatures of 160° F. In addition, clamp 20 must be able to withstand the same temperatures without being subject to corrosion or melting. Stainless steel is a good choice for clamp 20.

Figure 4B:
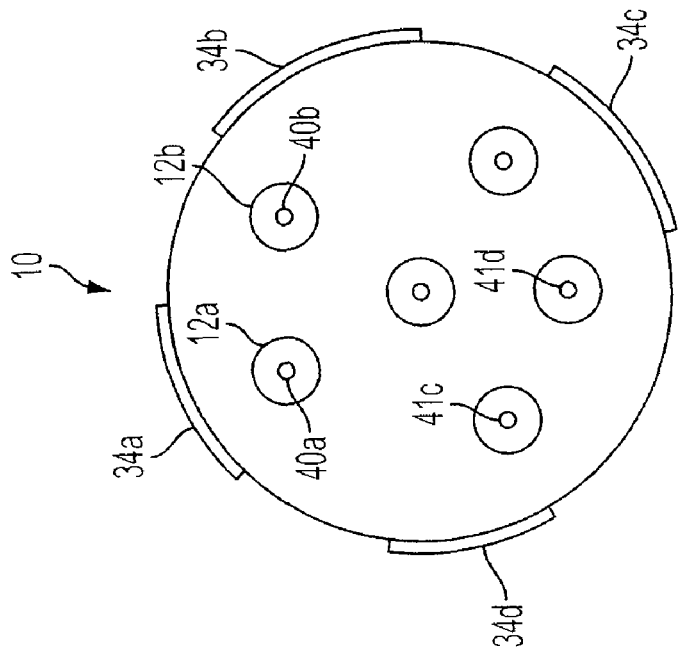
FIGS. 4A and 4B show cross-sections of the ionization vacuum gauge shown in FIG. 1 with different magnet configurations around the grid insulator posts, according to two exemplary embodiments of the invention.
Figure 4A:
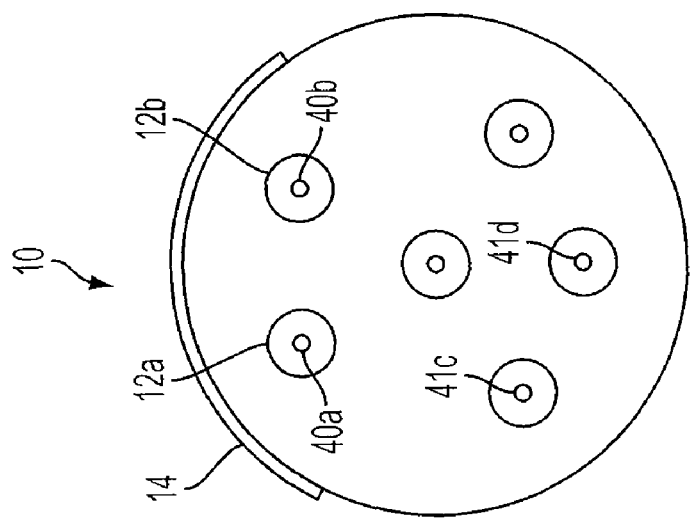

In another embodiment of the present invention, magnet 14 may wrap around the entire circumferential surface of tubular housing 18. As another embodiment, magnet 14 may be comprised of multiple small strips of magnets, oriented side-by-side, along the circumferential outer tubular surface of housing 18. Such an embodiment is shown in FIG. 4B, where four small magnetic strips 34a, 34b, 34c and 34d are oriented to fit around the outer tubular surface of housing 18.

It will be understood that the polar orientation of magnetic strips 34a-34d is north, south, north, south, etc., in sequence. Fewer or more numbers of magnetic strips 34 may be used by the present invention. Moreover, the magnetic strip may be made of any dimension in length and width, and of any thickness dimension.

The present invention may be used in any high vacuum system where metallic evaporates inside the vacuum system accumulate on the ion gauge collector, or grid insulators.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A vacuum gauge comprising
an ion collector wire extending longitudinally in a tubular section of a housing,
a filament extending longitudinally along and spaced from the ion collector wire,
a grid surrounding the ion collector wire,
grid insulators extending longitudinally in the tubular section of the housing including electrical conductors for providing a voltage potential to the grid, and
a magnet disposed externally to the tubular section of the housing,
wherein the magnet is positioned over a portion of the tubular section of the housing, directly over internal grid insulator posts, and
the magnet provides a shield surrounding the grid insulator posts.

2. The vacuum gauge of claim 1 wherein
the magnet is a flexible magnetic strip, and
positioned around the exterior of the tubular section of the housing.

3. The vacuum gauge of claim 2 wherein
the magnet is secured transversely to the grid insulators on the exterior of the tubular section of the housing.

4. The vacuum gauge of claim 3 wherein
a clamp provides a press fit for the flexible magnetic strip around the exterior of the tubular section of the housing.

5. The vacuum gauge of claim 1 wherein
an interior of the tubular section of the housing surrounds a Bayard-Alpert ionization gauge, and
the magnet is a flexible magnetic strip and is fastened to surround the Bayard-Alpert ionization gauge.

6. The vacuum gauge of claim 5 wherein
the flexible magnetic strip is oriented transversely and adjacent to the grid insulators.

7. The vacuum gauge of claim 6 wherein
the flexible magnetic strip includes a plurality of magnetized strips oriented circumferentially around the exterior of the tubular section of the housing.

8. The vacuum gauge of claim 5 wherein
the magnet includes a magnetic intensity of at least 160 gauss.

9. The vacuum gauge of claim 5 wherein
the magnet is fastened to the tubular section of the housing with a stainless steel hose clamp that is adjustable to provide a press fit between the magnet and the tubular section of the housing.

* * * * *